(12) United States Patent
Luke

(10) Patent No.: US 6,482,148 B1
(45) Date of Patent: Nov. 19, 2002

(54) OPTICAL SCOPE WITH MEASURING SYSTEM

(75) Inventor: Barry Edward Luke, Essex (GB)

(73) Assignee: Keymed (Medical & Industrial Equipment) Ltd., Essex (GB)

( * ) Notice: Subject to any disclaimer, the term of this patent is extended or adjusted under 35 U.S.C. 154(b) by 0 days.

(21) Appl. No.: 09/242,931
(22) PCT Filed: Jun. 23, 1998
(86) PCT No.: PCT/GB98/01831
§ 371 (c)(1), (2), (4) Date: Feb. 26, 1999
(87) PCT Pub. No.: WO99/00642
PCT Pub. Date: Jan. 7, 1999

(30) Foreign Application Priority Data

Jun. 27, 1997 (GB) .............................................. 9713680

(51) Int. Cl.[7] .................................................. A61B 1/07
(52) U.S. Cl. ........................................ 600/117; 600/149
(58) Field of Search ................................ 600/106, 117, 600/148, 167, 168

(56) References Cited

U.S. PATENT DOCUMENTS

| 3,595,220 A | 7/1971 | Kawahura |
| 3,804,081 A | 4/1974 | Kinoshita et al. |
| 3,817,619 A | 6/1974 | Kawahura |
| 3,817,631 A | 6/1974 | Kawahura |
| 3,817,635 A | 6/1974 | Kawahara |
| 3,819,267 A | 6/1974 | Kawahura |
| 4,271,829 A | 6/1981 | Heckele |
| 4,325,640 A | 4/1982 | Dreyfus et al. |
| 4,688,555 A | 8/1987 | Wardle |
| 4,896,343 A | 1/1990 | Saunders |
| 4,941,454 A * | 7/1990 | Wood et al. ................. 600/149 |
| 5,057,681 A | 10/1991 | Beder et al. |
| 5,111,056 A | 5/1992 | Yoshimura et al. |
| 5,268,687 A * | 12/1993 | Peled et al. .................. 346/108 |
| 5,431,645 A | 7/1995 | Smith et al. |
| 5,475,485 A | 12/1995 | Diener |
| 5,693,003 A | 12/1997 | Wölfelschneider et al. |

FOREIGN PATENT DOCUMENTS

| EP | 0060629 A1 | 9/1982 |
| EP | 0442393 A2 | 8/1991 |
| EP | 0552429 A1 | 7/1993 |
| GB | 2041690 A | 9/1980 |
| GB | 2173301 A | 10/1986 |
| WO | WO89/11630 | 11/1989 |
| WO | WO95/30126 | 11/1995 |

* cited by examiner

Primary Examiner—John Mulcahy
(74) Attorney, Agent, or Firm—Smith, Gambrell & Russell, LLP

(57) ABSTRACT

An optical scope for viewing a feature at an inaccessible location includes a tube having a distal end which is insertable in use into an inaccessible location and a proximal end connected to a housing. The tube contains an optical system for gathering an image of a feature and relaying the image to a viewer. The tube also contains a device for directing a laser beam to a first reference point in the distal end, a first reflector mounted in the distal end for rotation about the first reference point to change the direction of the laser beam so as to direct the beam out of the scope to a target feature, and a second reflector mounted in the distal end for rotation about a second reference point to change the direction of a reference axis intersecting the second reference point so as to cause the axis to intersect the laser beam at a target feature. The scope includes a control device actuable at the proximal end of the scope to rotate the first and second reflectors about the first and second reference points, position sensors for detecting movement of the first and second reflectors, and an antibacklash means associated with the control device.

29 Claims, 12 Drawing Sheets

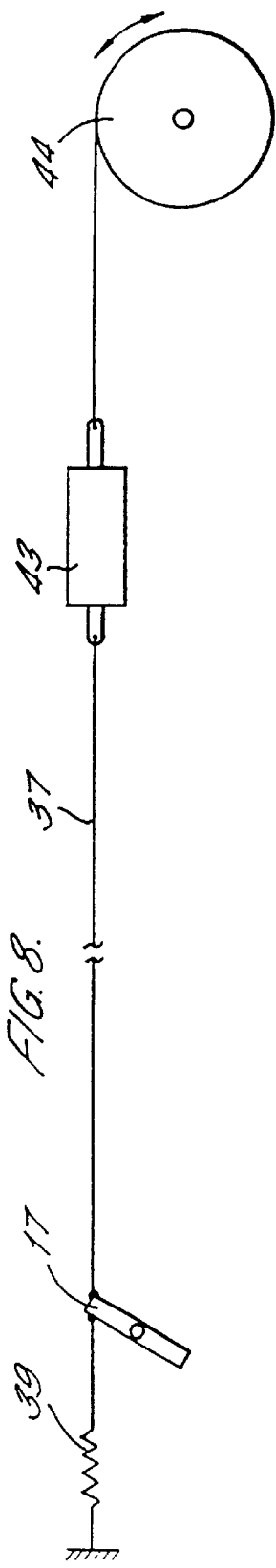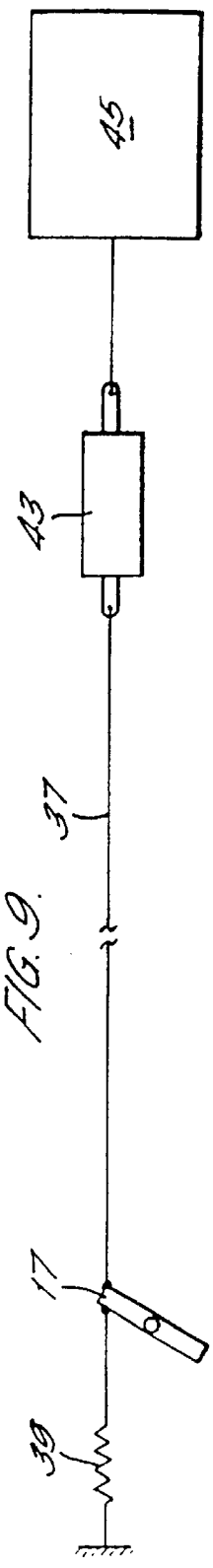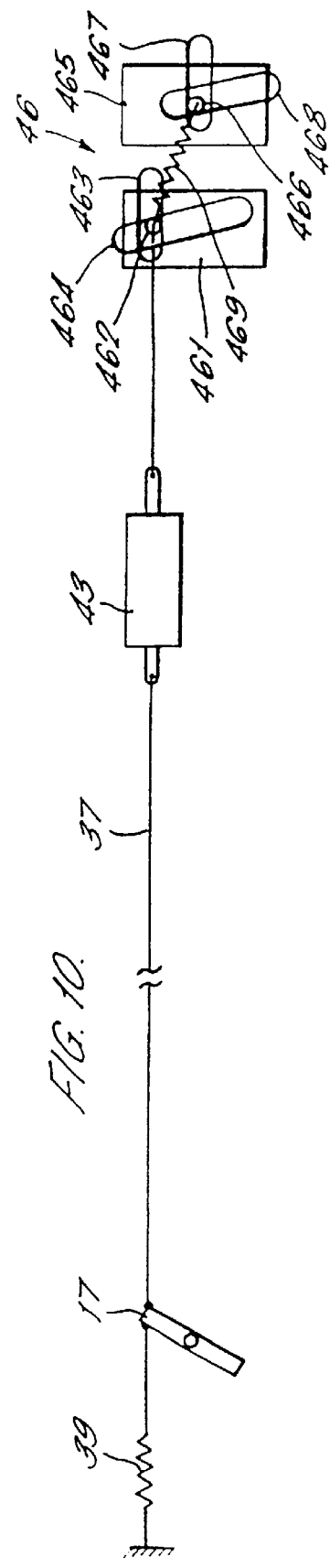

OPTICAL SCOPE WITH MEASURING SYSTEM

The present invention relates to optical scopes such as borescopes and endoscopes which include a system for measuring the dimensions of a remote or inaccessible feature which is viewed through the scope.

An example of this type of scope is described in International Patent Application WO96/20389. A typical application for such scopes is in the inspection of gas turbine engines. The scope can be used to inspect the condition of components such as turbine blades to see whether there are any faults which require the engine to be stripped down in order to access the blades for repair or replacement. Systems which allow a feature viewed through the scope to be measured have been developed so that the seriousness of any faults which are seen can be assessed. If the size of the fault is within a particular range, it may be unnecessary to repair or replace the blade and an engine strip down would not therefore be required. Thus, scopes which enable dimensions of features viewed through them to be accurately measured can dramatically reduce the time and cost of operations such as engine inspection.

The system described in WO96/20389 determines the dimensions of a feature on the basis of the distance of the feature from the scope (the object distance) and the magnification of the scope. The object distance is determined by means of the focus control. An image of the feature is brought into sharp focus and a high resolution encoder associated with the focus control is used to determine the focus position. A processor then converts the focus position data into an object distance signal.

A problem with this system is that it is subjective because different operators may consider that the image is in focus at slightly different positions of the focus control. This leads to inaccuracy and inconsistency in determination of the object distance.

A number of systems currently exist which use the principals of triangulation to measure features and contours on an item. For example, European patent 0442393 uses a pair of lasers to measure by triangulation the contours of vehicle body panels. Similarly, U.S. Pat. No. 4,325,640 uses laser triangulation for measuring the contours of helicopter rotor blades. However, such systems rely on the workpiece to be measured being readily accessible so that the measuring system can be moved freely around it.

The present invention provides an optical scope for viewing and determining a dimension of a feature at an inaccessible location, comprising a tube having a distal end which is insertable in use into an inaccessible location and a proximal end connected to a housing; an optical system for gathering an image of a feature and relaying the image to a viewing means; means to direct a laser beam to a first reference point in the distal end of the cube; a first reflector mounted in the distal end of the tube for rotation about the first reference point and being operable to change the direction of the laser beam so as to direct the beam out of the scope to a target feature; a second reflector mounted in the distal end of the tube for rotation about a second reference point and being operable to change the direction of a reference axis intersecting the second reference point so as to cause the axis to intersect the laser beam at the target feature; control means actuable at the proximal end of the scope to rotate the first and second reflectors about the first and second reference points; position sensing means to detect movement of the first and second reflectors, and antibacklash means associated with the control means.

Preferably, the control means for each reflector comprises a mechanical linkage extending between the reflector and a rotatable control collar mounted on the housing.

The mechanical linkage preferably comprises a pullwire.

Conveniently, the antibacklash means comprises spring means biasing each reflector in opposition to the control means.

The antibacklash means further may comprise a friction braked wheel to which the proximal end of the pullwire is secured.

Alternatively, the antibacklash means may further comprise a recirculating ball screw device to which the proximal end of the pullwire is secured.

In another alternative, the antibacklash means further comprises a first cylinder located, and constrained to move axially, in the housing and to which the proximal end of the pullwire is secured, a second cylinder located proximally of the first cylinder and also constrained to move axially, spring means urging the first and second cylinders towards each other, a rotatable actuating collar linked to the first and second cylinders to move the cylinders axially upon rotation of the collar and spring means urging the collar axially against a fixed part of the housing.

In yet another antibacklash system, the pullwire is loosed around a wheel, whose axis is spring biased in the proximal direction, to provide two pullwire limbs, the first limb is attached to the reflector on one side of its pivot point, the second limb is attached to the reflector on the other side of its pivot point and first and second position sensing means are associated with the first and second limbs respectively.

In a preferred embodiment, the optical scope further comprises means to direct a second laser beam to the second reference point, whereby the reference axis is defined by the second laser beam.

In another embodiment, the scope has a viewing axis intersecting the second reference point whereby the reference axis is defined by the viewing axis.

In this case, a graticule may be mounted in the image transmission system, whereby when an image of a feature is aligned with the centre of the graticule the viewing axis is positioned so as to intersect the feature.

Preferably, the means to direct the first laser beam to the first reference point comprises at least one optical fibre and may further comprise at least one reflector mounted in the path of the beam.

Preferably, the means to direct the second laser beam to the second reference point comprises at least one optical fibre and may further comprise at least one reflector mounted in the path of the beam.

Conveniently, the position sensing means is located in the housing and may comprise a linear voltage displacement transducer, a Moire fringe device, a variable resistor potentiometer, a variable reluctance transformer, or an inductosyn.

In another aspect, the invention provides apparatus for determining a dimension of a feature at an inaccessible location, comprising an optical scope of the aforementioned type, viewing means for receiving an image relayed by the optical system of the optical scope and processing means for receiving data from the position sensing means and calculating a dimension of the feature from the data.

The viewing means preferably comprises a camera and a monitor for displaying the image received by the camera.

The invention will now be described in detail, by way of example only, with reference to the accompanying drawings in which:

FIG. 8 is a schematic diagram of a first antibacklash system for use in the embodiment of FIG. 6;

FIG. 9 is a schematic diagram of a second antibacklash system;

FIG. 10 is a schematic diagram of a third antibacklash system;

Figure 15:
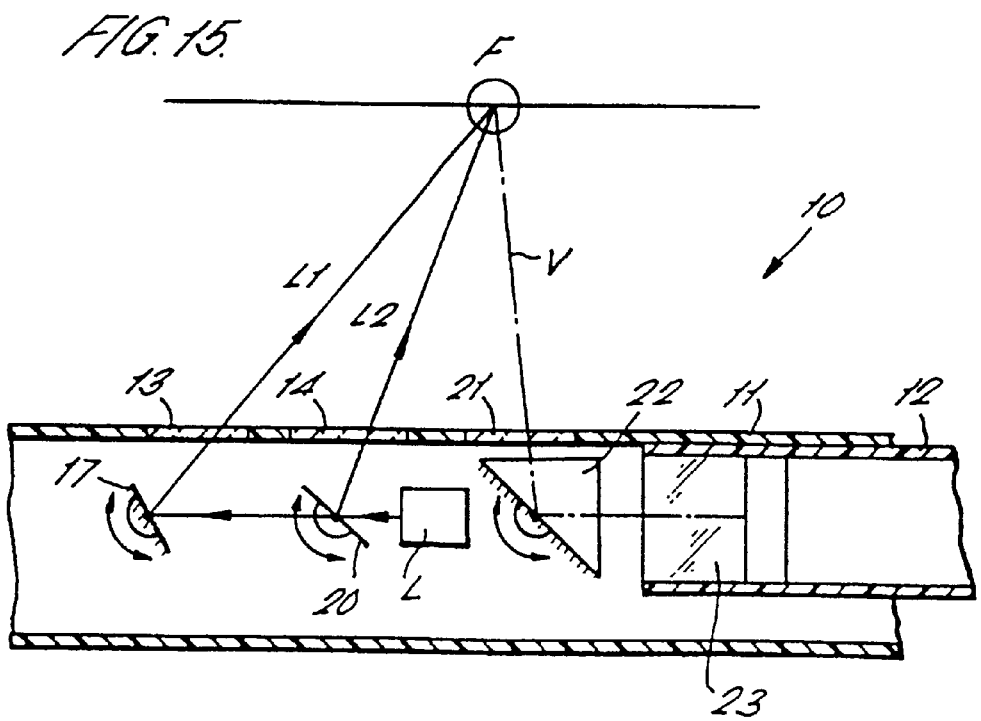
Figure 16:
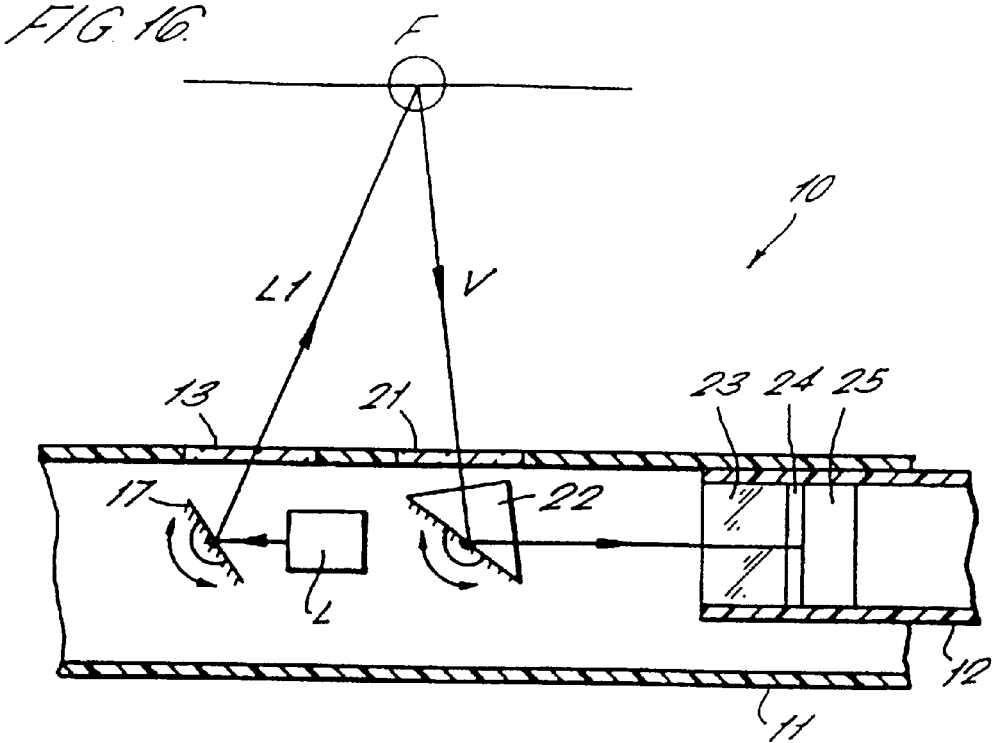
Figure 17:
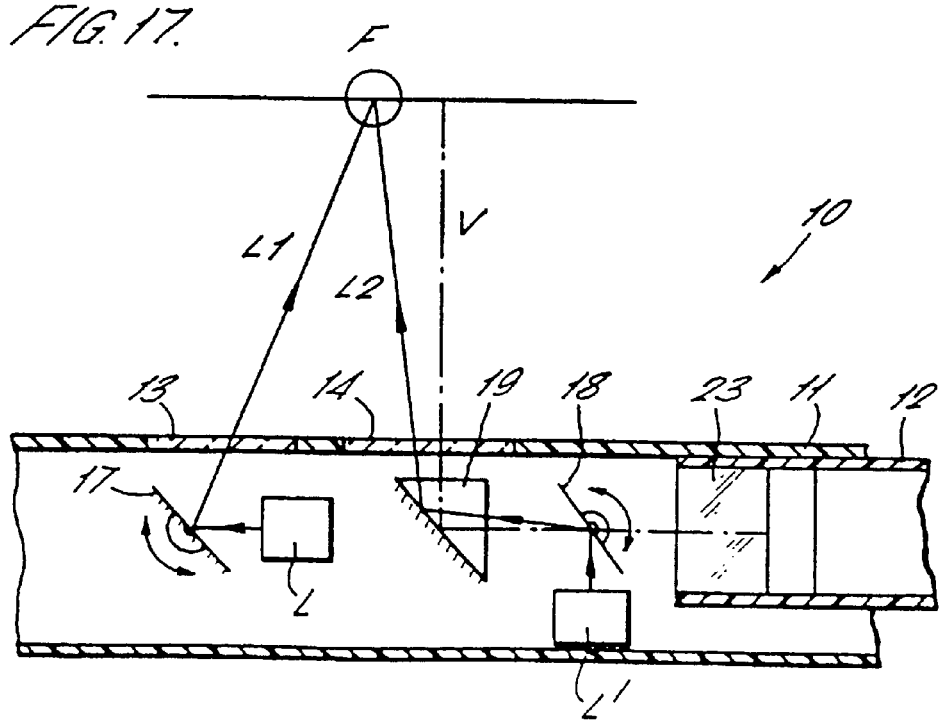
Figure 18:
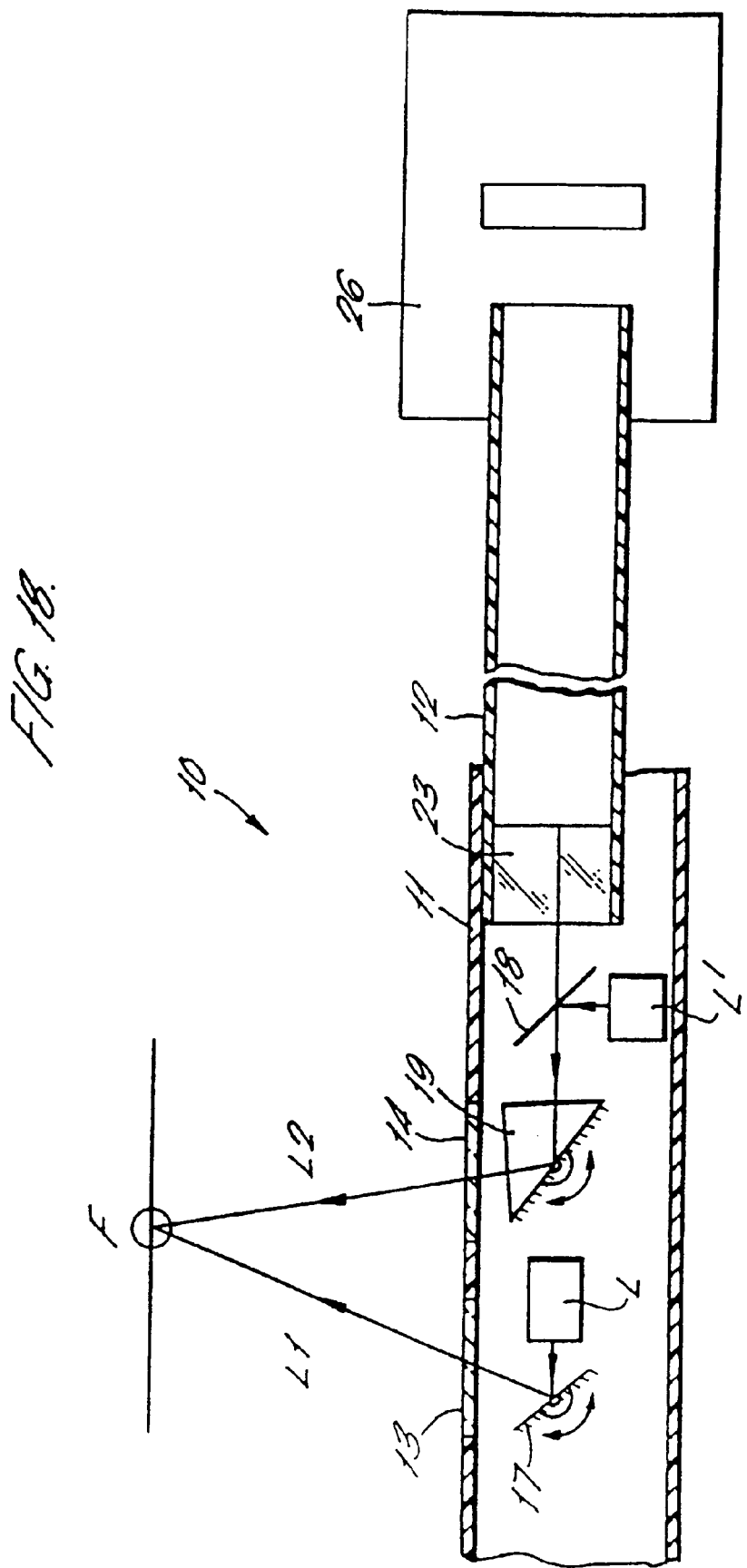

FIG. 15 likewise shows a third embodiment of the invention;

FIG. 16 likewise shows a fourth embodiment of the invention;

FIG. 17 likewise shows a fifth embodiment of the present invention using two separate laser sources; and FIG. 18 likewise shows a sixth embodiment of the invention also using two separate laser sources.

Referring now to FIGS. 1 to 5, these diagrams illustrate how the basic principles of triangulation are utilised by the present invention in order to determine various dimensions of a feature. Details of the scope construction are described more fully below in connection with FIGS. 6 to 18.

The invention employs a beam of laser light L1 which is directed through an optical scope to a first reference point located in the distal end of the scope, and from the reference point out of the scope towards a target feature F. When the laser beam hits the target feature it appears as a spot of light which can be viewed through the scope.

A second laser beam L2 is also directed through the scope to a second reference point defined in the scope. This second reference point is spaced from the first so that they define a datum line R. The position of the first and second reference points depends upon the design of the scope and thus the separation S of the two laser beams L1,L2 at the datum line R can be fixed at a known value.

Figure 1:
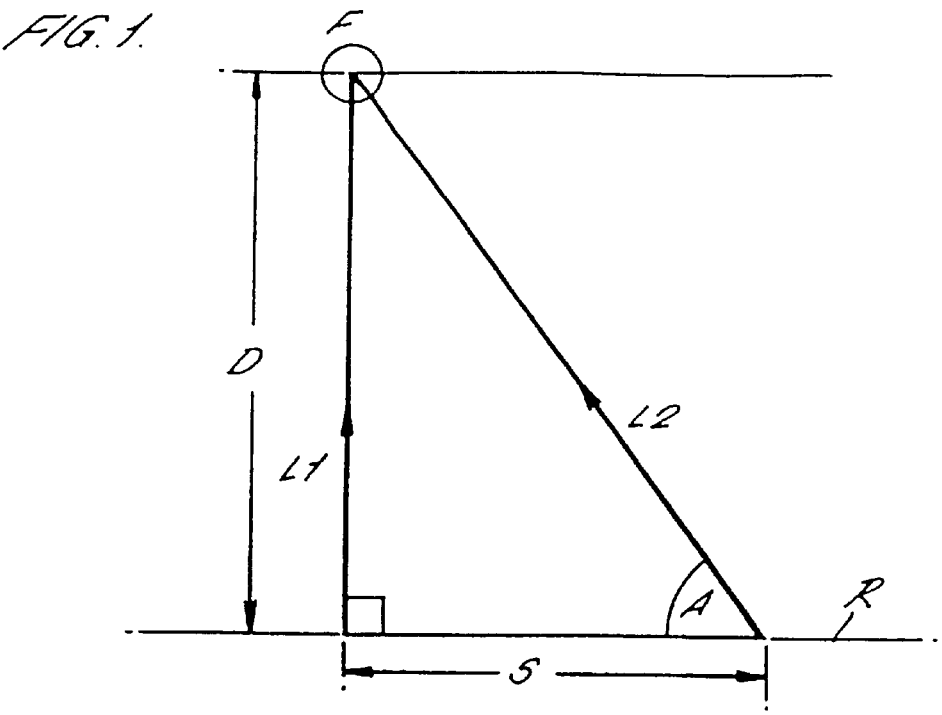
FIG. 1 is a diagram illustrating the basic principles of the invention used to determine an object distance.

In FIG. 1, the first beam L1 is in a fixed position perpendicular to the datum line R.

From the second reference point the second laser beam L2 is also diverted out of the scope. The direction of the beam L2 can be altered to cause it to intersect the first laser beam L1 at the point at which it hits the target feature F.

Thus, the second beam L2 can be steered so as to alter its angle relative to the datum line R. When the second beam L2 intersects the first laser beam L1 at the feature F the spot of light produced by L2 is coincident with that of L1 on the feature F. This position is easy to identify when observing an image of the feature F through the scope. When this position is reached, the angle A of the second beam L2 relative to the datum line R is determined. Once the angle A is known, and given that the separation S of the two beams L1 and L2 at the datum line R is also known, the distance D travelled by the first beam L1 Prom the datum line R to the feature F, i.e the object distance, can be calculated according to the following simple equation:

$$D = \tan A \times S$$

Figure 2:
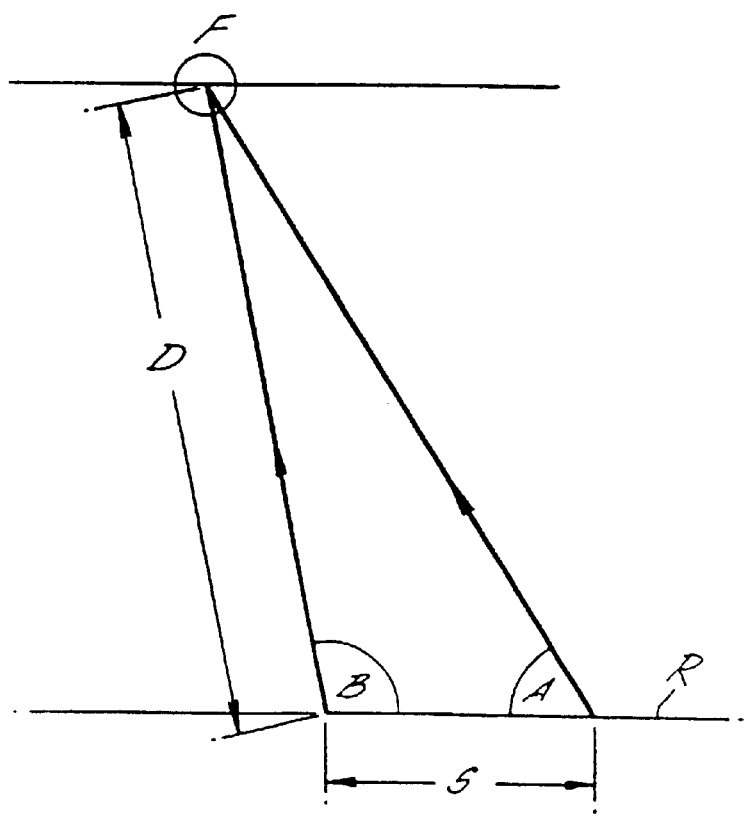
FIG. 2 is a diagram illustrating an alternative manner of determining an object distance.

In practice, it may not be convenient for the first beam L1 to be in a fixed position relative to the datum line R because it may be difficult to manoeuvre the scope to ensure that the fixed beam hits the desired target feature F. Therefore, it is preferable if the first beam L1 can be steered, as well as the second beam L2. This arrangement still allows the object distance D to be calculated by measuring the angle B of the first beam L1 relative to the datum line R, in addition to the angle A of the second beam L2, as illustrated in FIG. 2.

When the two beams L1 and L2 are coincident on the target feature F the angles A and B are measured (and the separation S of the two beams L1 and L2 at the datum line is already known). From this data, the object distance D can be calculated as follows:

$$D = \frac{S \times \sin A}{\sin(180 - (A+B))}$$

A system employing two steerable beams of laser light can also be used to directly measure the depth and width of the target feature and to plot its profile.

Figure 3:
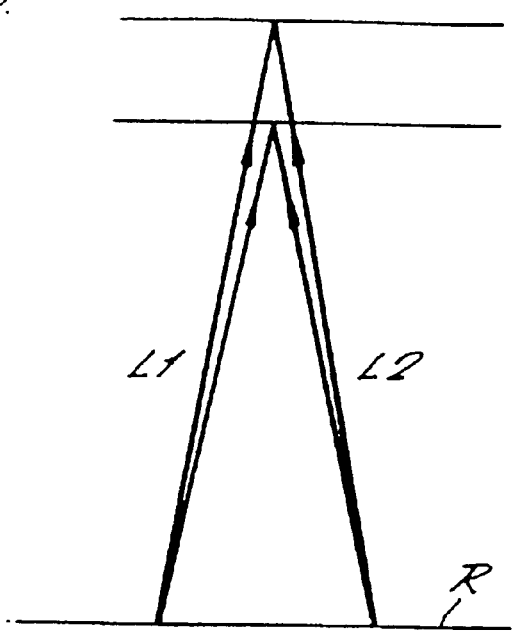
FIG. 3 is a diagram illustrating the basic principles of depth measurement of a feature.

FIG. 3 illustrates how the depth of a feature F can be measured. As shown, the two beams L1 and L2 are adjusted to intersect at a first point of a feature F and the object distance D1 is calculated as described above. The beams L1 and L2 are then moved so as to intersect at a second point on the target feature and this object distance D2 is also determined. The difference between the two object distances thus represents the depth of the feature F between the first and second points.

Figure 4:
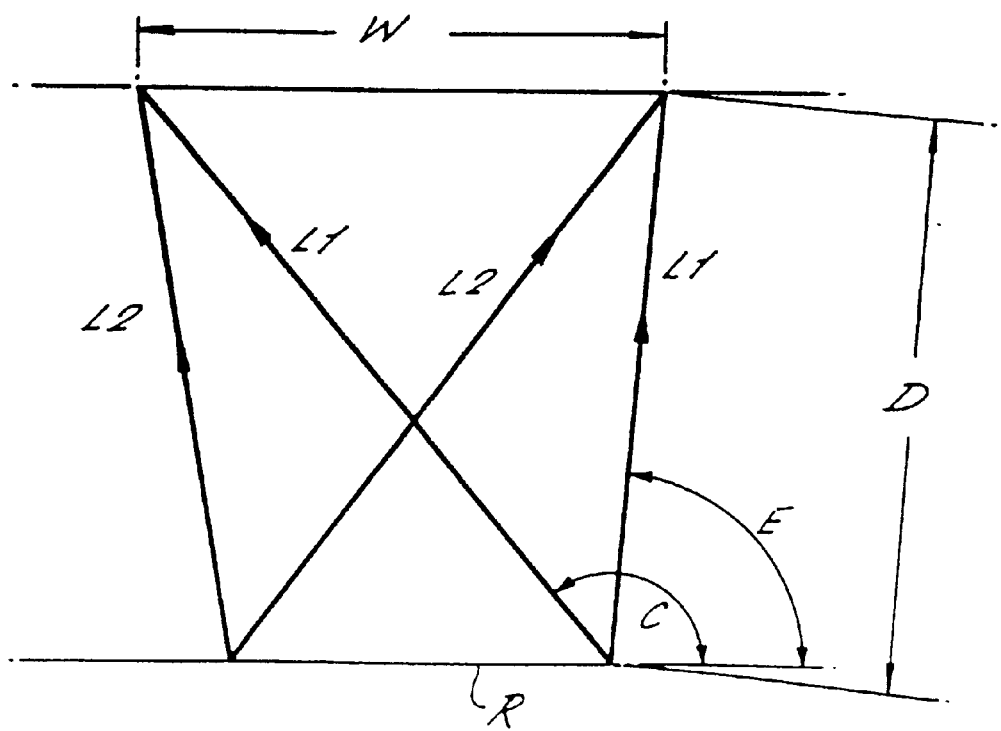
FIG. 4 is a diagram illustrating the basic principles of width measurement of a feature.

FIG. 4 illustrates how the width W of a feature can be measured. In this case, the two beams L1 and L2 are adjusted to intersect a first point on one side of the target feature and then at a second point on the other side. The angles C and E of the first beam L1 relative to the datum line R when the beam L1 strikes the first and second points of the feature F respectively are measured and the object distance D for the second point is determined in the manner described above. Using this data, the width W of the feature F can be calculated from the following equation:

$$W = \frac{D \times \sin(C-E)}{\sin(180-C)}$$

Figure 5:
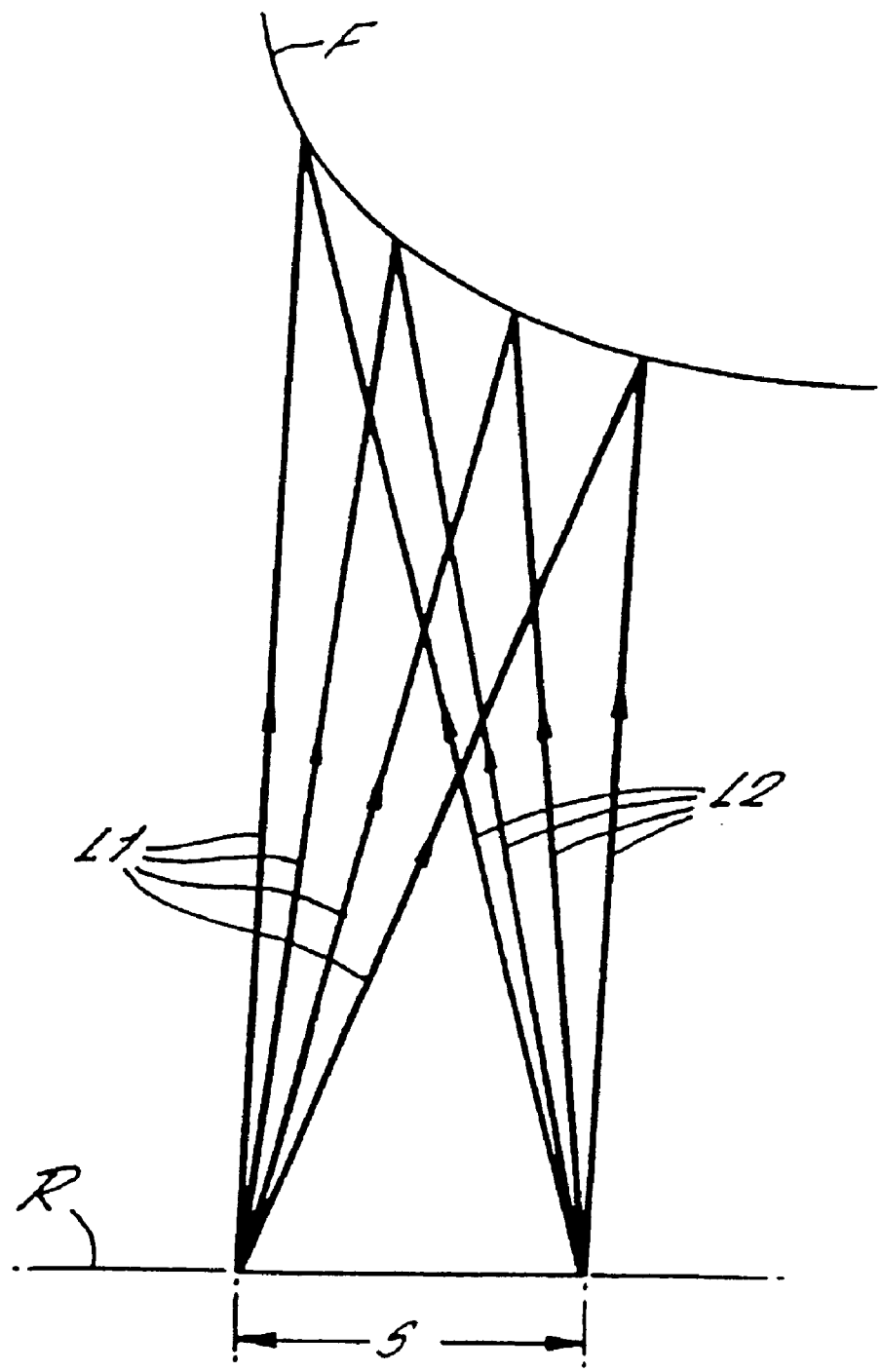
FIG. 5 is a diagram illustrating the basic principles of profile capture of a feature.

Furthermore, the object distance and width determinations can be combined in order to track the profile of a feature F as indicated in FIG. 5, by adjusting the two beams L1 and L2 so as to intersect at a series of discrete points at intervals across the feature. At each point the object distance is calculated and the width between adjacent points is also determined. These two measurements can be combined in order to produce a plot of the profile of a feature. Thus, the curvature of an item such as a turbine blade can be determined.

Practical embodiments of the invention showing how apparatus utilising the principles explained above can be incorporated into an optical scope will now be described with reference to FIGS. 6–18.

Figure 6:
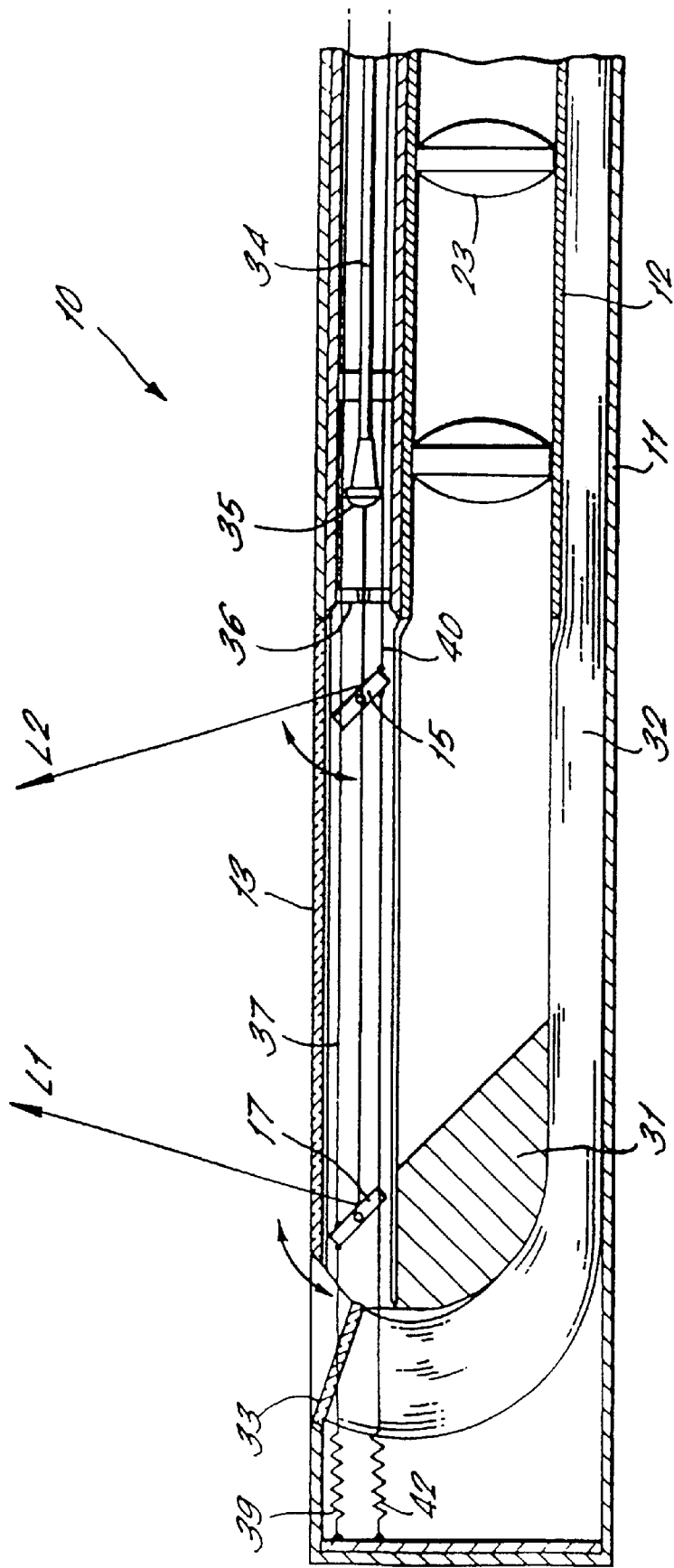
FIG. 6 shows in cross section, the distal end of a scope in accordance with a first embodiment of the present invention.
Figure 7:
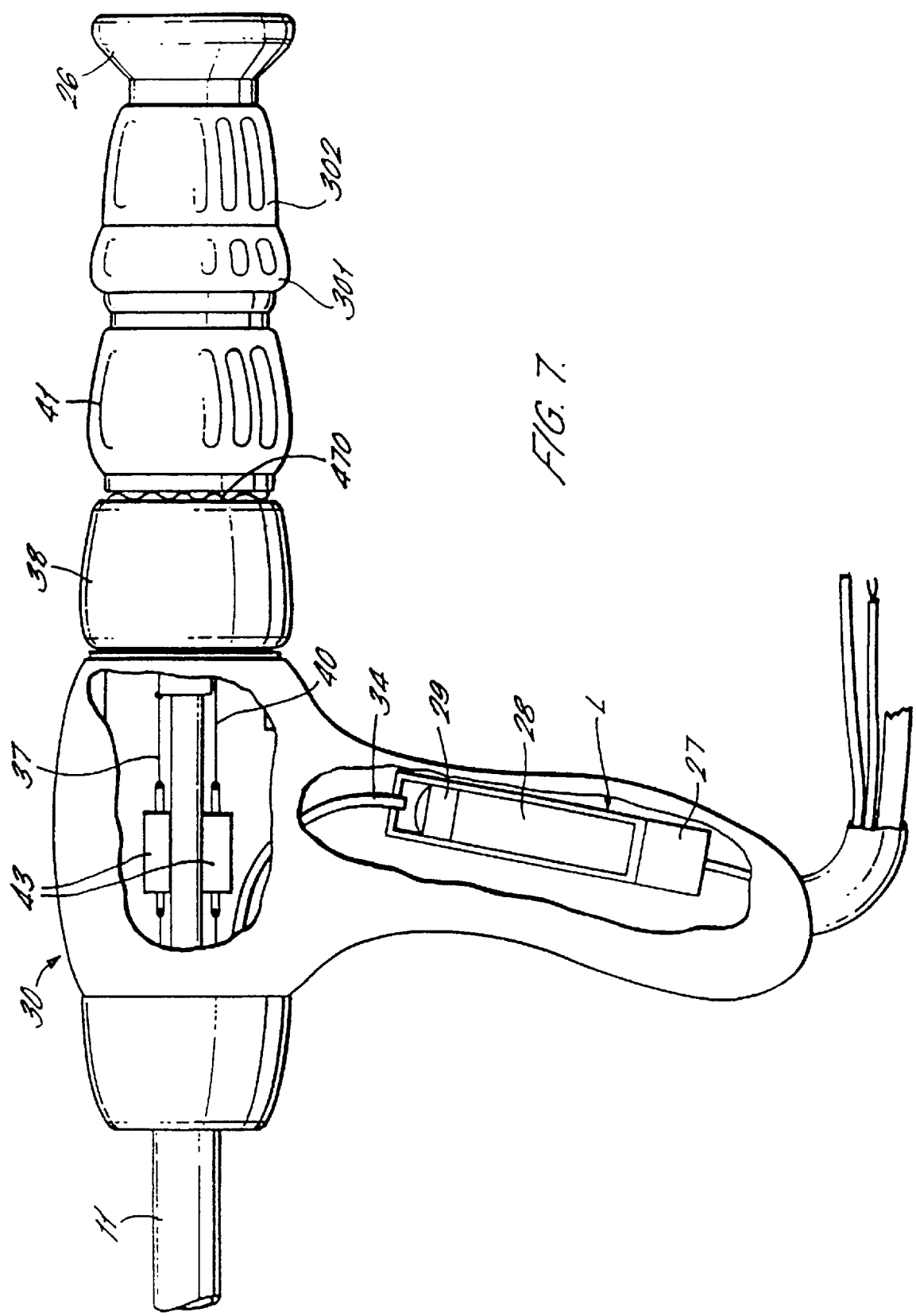
FIG. 7 is part cutaway view of the housing at the proximal end of the tube shown in FIG. 6.

A first preferred embodiment of optical scope 10 incorporating a measuring system in accordance with the present invention is illustrated in FIGS. 6 and 7.

The scope 10 consists of a conventional insertion tube 11, which in use is inserted into a remote or inaccessible location. In FIG. 6, only the distal end of the insertion tube 11 is shown. The proximal end of the insertion tube 11 is connected to a housing 30, described further below and shown in FIG. 7. In this example the scope 10 is a borescope with a rigid insertion tube 11, although an endoscope with a flexible insertion tube may also be used. Within the insertion tube 11, an inner tube 12 contains a conventional image transmission system.

This system may consist of a series of lenses 23 or optical fibres, which transmit an image to viewing means such as an eyepiece or camera attachment (shown schematically as reference number 26 in FIG. 7) located at the proximal end of the scope 10. Alternatively, the image transmission system may be electronic rather than optical, with a device such as an image-to-video converter located in the distal end of the inner tube 12 (as shown by reference number 25 in FIG. 16)

In this example, the scope 10 is of the orbital scanning type, which is designed for viewing objects positioned laterally with respect to the longitudinal axis of the insertion tube 11. Accordingly, a lateral viewing window 13 is provided in the distal end of the insertion tube 11. A reflector 31 is provided to divert an image of a laterally viewed feature into the image transmission system 23. A bundle of optical fibres 32 is provided to transmit light from a conventional light source at the proximal end of the scope 10 to illuminate the field of view of the scope 10 through an illumination window 33. The insertion tube 11 is rotatable about its longitudinal axis by means of a rotatable scan control collar 301 mounted on the housing 30. An image viewed through the scope 10 is focused in a conventional manner by a focus control collar 302 also mounted on the housing 30.

A single laser source L is associated with the scope 10. In this embodiment, as shown in FIG. 7, the laser source L is located in the housing 30 at the proximal end of the scope 10. The laser source L in this example consists of a laser diode power supply 27, a visible laser diode module 28 for producing the laser and a lens 29. The laser beam produced is transmitted through the scope 10 to the distal end by a single filament optical fibre 34. The divergent laser beam which is emitted from the distal end of the fibre 34 is focussed into a narrow beam by a suitable lens 35. The focussed beam passes through an aperture in a mask 36 which prevents unwanted light entering the system. The aperture is sufficiently large to avoid diffracting the focussed laser beam.

Alternatively, the laser source L could be positioned within the insertion tube 11 in the vicinity the distal end as shown schematically in later embodiments, or it may be located at any position along the insertion tube 11 or even outside the scope 10, whichever is convenient.

The single laser beam produced by the source L is split into two separate beams L1 and L2 by a conventional beam splitter/reflector device 15 which is pivotally mounted in the path of the beam. A beam splitter typically consists of a reflector with a special coating which allows half of the light incident upon it to be transmitted through the device while the remainder is reflected from it in a conventional manner.

The first laser beam L1 passes through the beam splitter 15 and strikes a pivotally mounted reflector 17. The reflector 17 may consist of a mirror as shown, or a prism.

Control means is provided to enable a user to steer both the beam splitter 15 and the reflector 17 by tilting them about their respective pivot points as shown in FIG. 6 by the double headed arrows. Referring first to the reflector 17, to accomplish this, a mechanical linkage, preferably a pullwire 37, is attached to one side of the reflector 17. The pullwire 37 extends through the insertion tube 11 into the housing 30 where it is connected to a rotatable control collar 38 (see FIG. 7). Rotation of the collar 38 in one direction retracts the pullwire 37 to pivot the reflector 17 one way and rotation in the other direction lets out the pullwire 37 to allow the reflector 17 to pivot the other way. The reflector 17 is also biased by spring means such as a coil spring 39 one end of which is attached to the reflector 17 on the same side of the pivot point as the pullwire 37. The other end of the coil spring 39 is secured to the distal end of the scope 10. Thus, the spring 39 tensions the pullwire 37 and assists in accurately moving the reflector 17.

Similarly, the beam splitter 15 is provided with a pull wire 40 connected to a separate control collar 41 and biased by a spring 42, allowing it to be pivoted in the same manner.

For clarity and convenience in FIG. 6 the pullwire 37 and spring 39 are shown attached to the upper edge of the reflector 17 while the pullwire 40 and spring 42 are shown attached to the lower edge of the beam splitter 15. However, this arrangement may be reversed or otherwise altered to suit the space constraints within the insertion tube 11.

Position sensing means are associated with the control means to detect movement of the pullwires 37, 40 and hence to allow the angular positions of the beam splitter 15 and the reflector 17 relative to a datum line R defined by the two pivot points to be determined.

In this embodiment, the position sensing means comprises a linear voltage displacement transducer (LVDT) 43 attached to each pull wire 37,40 in the housing 30 at the proximal end of the scope 10 as shown in FIG. 7. In an LVDT device, a core of magnetic material is movable through a series of coils, thereby causing changes in the current induced in the coils. These changes can be decoded to represent the degree of movement of the core.

The control means described above may suffer backlash problems which lead to inaccuracy in the measurements obtained from the position detectors 43. Accordingly, an antibacklash device is incorporated into the scope 10 in order to minimise this problem. The following examples of antibacklash devices are illustrated with reference to the reflector 17 but are also usable on the beam splitter 15 (or any other pivotable element whose position is to be measured).

A first embodiment of a suitable antibacklash device is illustrated schematically in FIG. 8. As described above, the reflector 17 is attached to a spring 39 secured to the distal end of the scope and to a pullwire 37 which extends through the insertion tube into the housing 30. The LVDT 43 is attached to the pullwire 37 in the housing 30. The proximal end of the pullwire 37 is secured to a friction braked control wheel 44 which is connected in any appropriate manner to the control collar 38 so as to be rotatable with the collar 38.

FIG. 9 shows in schematic form an alternative antibacklash device. Once again the reflector 17 is connected to a spring 39 secured to the distal end of the scope 10 and to a pullwire 37 which extends through the insertion tube 11 into the housing 30, where an LVDT 43 is located. The proximal end of the pullwire 37 is then connected to a conventional recirculating ball screw device 45 to combat backlash.

Yet another alternative antibacklash device is shown schematically in FIG. 10. This is similar to the previous antibacklash devices except that in this case the proximal end of the pullwire 37 is connected to an antibacklash mechanism 46 similar to that described in GB 2304920.

In the antibacklash mechanism 46, the pullwire 37 is secured to a first cylinder 461 which is axially slidable within the housing 30 but is not rotatable. A pin 462 projects radially from the first cylinder 461 and extends through an axial slot 463 which is formed in the housing 30. The pin 462 projects further to engage in a first helical slot 464 formed on the interior surface of the control collar 38 which is rotatably mounted on the housing 30. This mechanism ensures that when the control collar 38 is rotated, the cylinder 461 and hence the pullwire 37 are moved axially but do not rotate.

A second cylinder 465 is also located in the housing 30, proximally of the first cylinder 461. The second cylinder 465 also includes a radially projecting pin 466 which extends through an axial slot 467 in the housing 30 and into a second helical slot 468 formed in the interior surface of the control collar 38. The two pins 462 and 466 are linked together by a spring 469 which urges the first and second cylinders 461,465 together. In addition, another spring 470 (best seen in FIG. 7) biases the collar 38 distally against a fixed part of the housing 30.

Figure 11:
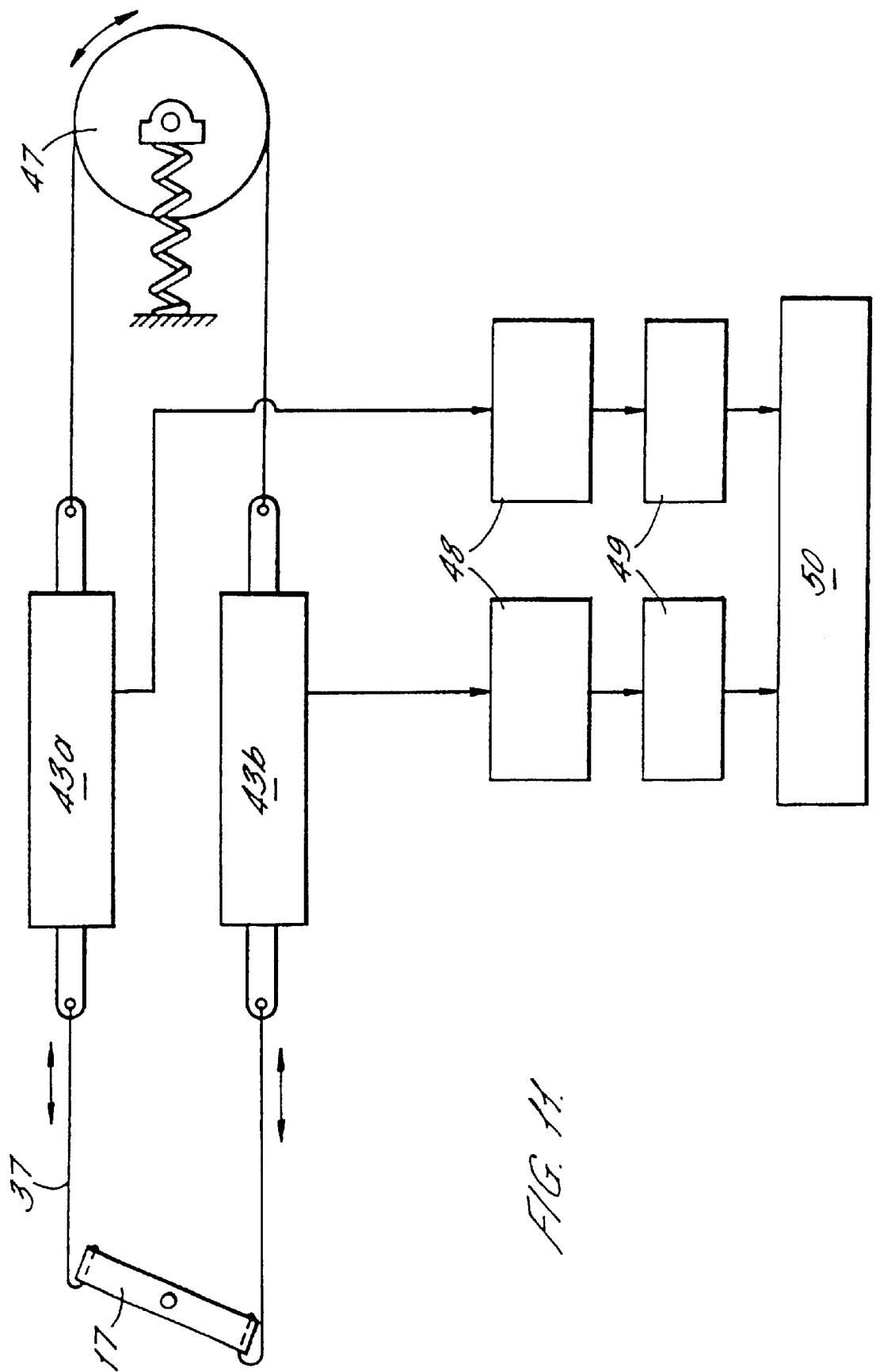
FIG. 11 is a schematic diagram of a fourth antibacklash system.

Yet another form of antibacklash device is illustrated in FIG. 11. In this case, the reflector 17 is not biased by a spring 39. Instead, each side of the reflector 17 is connected to an end of the pullwire 37 which extends through the insertion tube 11 into the housing 30 and is looped around a control wheel 47 whose axis is spring biased in a proximal direction as shown to tension the pullwire 37. An LVDT 43a,43b is associated with each leg of the pullwire 37. In this case, the signal from each LVDT 43a,43b is passed through a suitable decoder 48 and analog to digital converter 49 to a computer 50. Data relating to the position of the reflector 17 is then determined by subtraction of the signal from one LVDT 43a from the signal from other LVDT 43b.

When the scope 10 of FIGS. 6 and 7 is in use, the first laser beam L1 which has passed through the beam splitter 15 strikes the reflector 17 at its pivot point and is reflected so as to exit the insertion tube 11 through the window 13. The position of the reflector 17 is adjusted by the control means until the laser beam L1 strikes a target feature F at a desired location.

The second laser beam L2 is diverted by the beam splitter 15 out of the scope 10 through the window 13 towards the target feature F.

As mentioned above, the first and second laser beams L1 and L2 each strike their respective pivotable reflectors 15,17 at the point about which the reflectors pivot. Accordingly, the pivot points define the first and second reference points from which the two beams L1,L2 are directed to the target feature F. The distance between these pivot points is fixed at a predetermined value depending upon the design of the scope 10, and this is the separation S for use in the calculations described above. The pivot points also define the datum line R with respect to which the angles of the two laser beams L1,L2 are measured.

Figure 13:
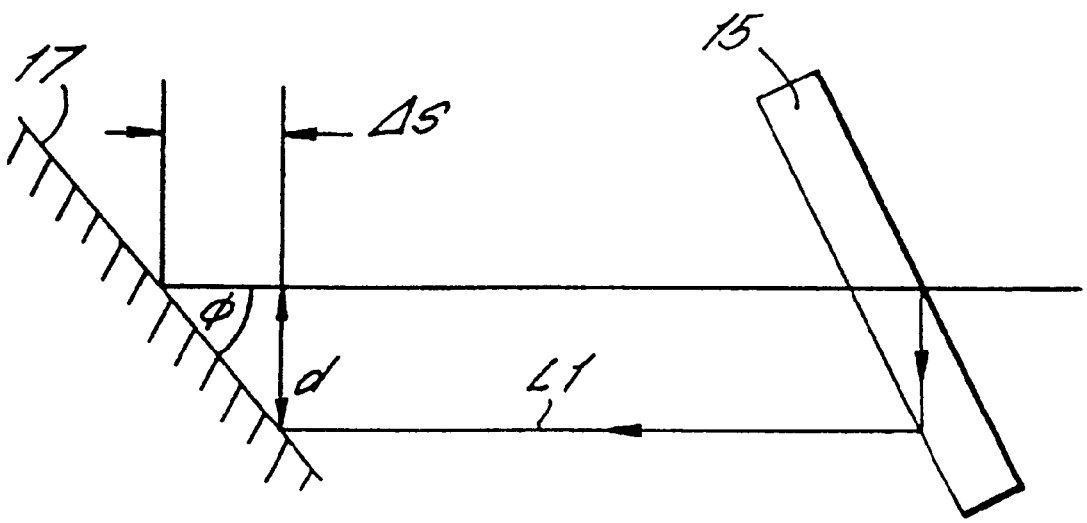
FIG. 13 is a diagram illustrating how a laser beam passes through a beam splitter.

In fact, the first laser beam L1 does not pass straight through the beam splitter 15 due to the finite thickness of the beam splitter 15 and the difference between its refractive index and that of air. This causes the beam L1 to be slightly displaced by a distance d as shown in FIG. 13 and this will affect the actual point at which the beam L1 impinges on the reflector 17 and hence the actual separation S between the two beams L1 and L2 required for the calculations described above. Therefore, the separation S is no longer simply the distance between the pivot points of the two reflectors 15,17, but is that distance minus $\Delta s$. Since knowledge of this separation is crucial to accurately calculating dimensions of a feature, it is necessary to compensate for this error.

$\Delta s$ can be calculated from the formula $$\Delta s = d \times \tan \phi$$

where $\phi$ is the angle of the reflector 17 relative to the datum line R, which is determined from the position data provided by the position detector 43, and d is determined in a known manner based upon the refractive index of the material used to make the beam splitter 15.

Figure 12:
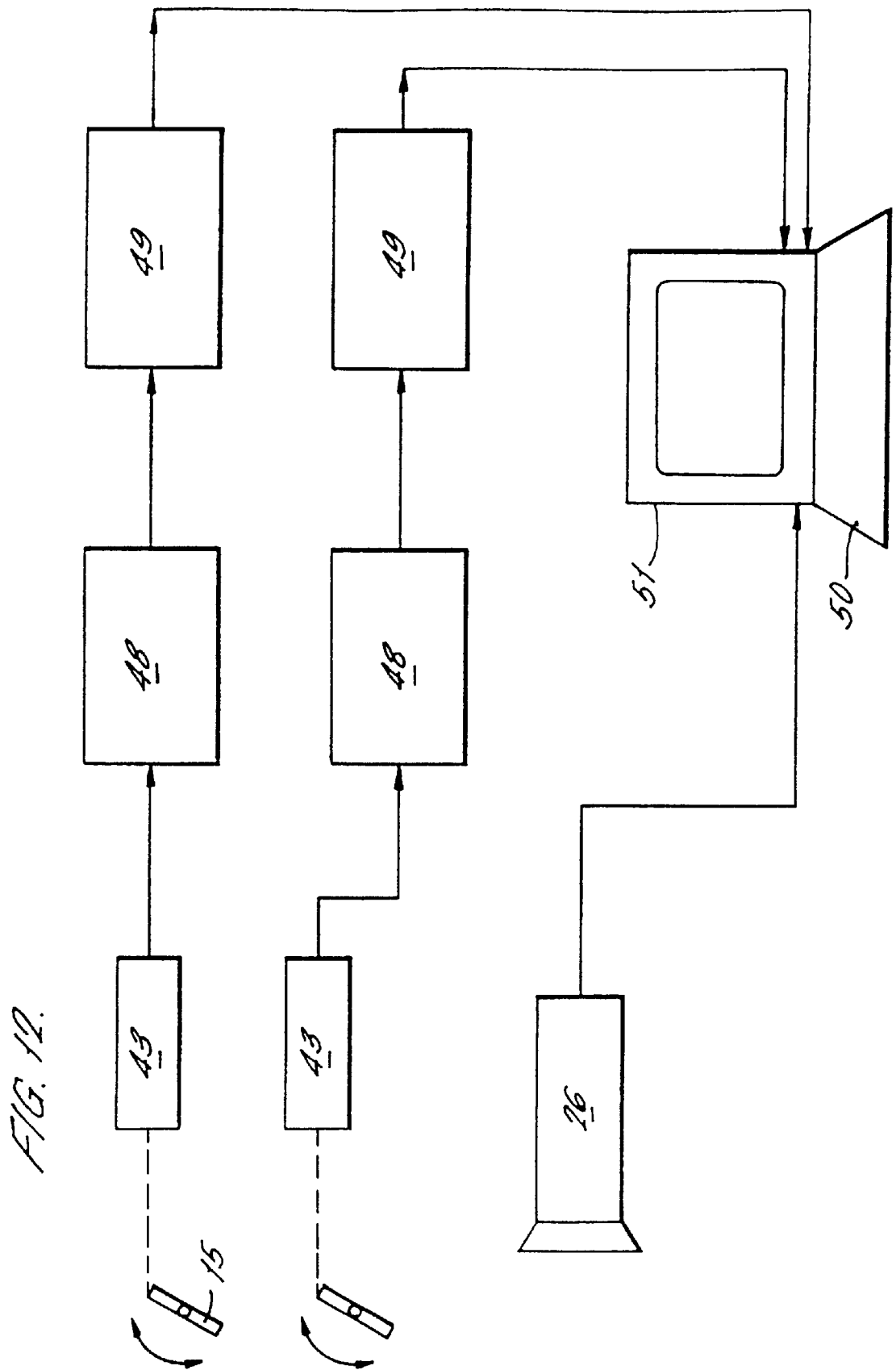
FIG. 12 is a schematic view of a measuring system incorporating an optical scope in accordance with the present invention.

In use, the beam splitter 15 and reflector 17 are adjusted until the two laser beams L1,L2 intersect when they strike the target feature F. The target feature F is observed through the window 13. Light received through this window 13 is diverted by the reflector 31 into the image transmission system 23 in the inner tube 12 for transmission to the viewing means 26. Typically the viewing means 26 will comprise a camera which will provide an image for viewing on the monitor 51 of the computer 50 as shown in FIG. 12.

Movement of the pullwires 37,40 is detected by the two LVDT's 43. This data is transferred via decoders 48 and analog to digital converters 49 to a computer 50, which is located externally of the scope 10, to enable the angles of the two reflectors 15,17 relative to the datum line R when the two laser beams L1,L2 have been positioned as desired on the target feature F to be calculated. Based upon this information, the required dimensions of the feature may be calculated by the processing means in the manner described above with reference to FIGS. 1–5.

In addition to potential backlash problems, the accuracy obtained from the apparatus of the present invention may also be adversely affected by changes in temperature which result in variations in the length of the control means operating the pivotable reflectors. These variations can be compensated for by including temperature sensors (not shown) within the scope 10. The processing means can make use of temperature information from such sensors to determine a correction value to apply to measurements which are taken. Alternatively, the control means can be produced from certain materials, or combinations of various materials which have different (or opposite) coefficients of expansion to offset temperature induced errors.

A number of alternative embodiments of optical scope 10 are illustrated schematically in FIGS. 14–18 where like reference numerals are used for corresponding parts where appropriate. In these simplified diagrams the control means and antibacklash devices are omitted for clarity.

Figure 14:
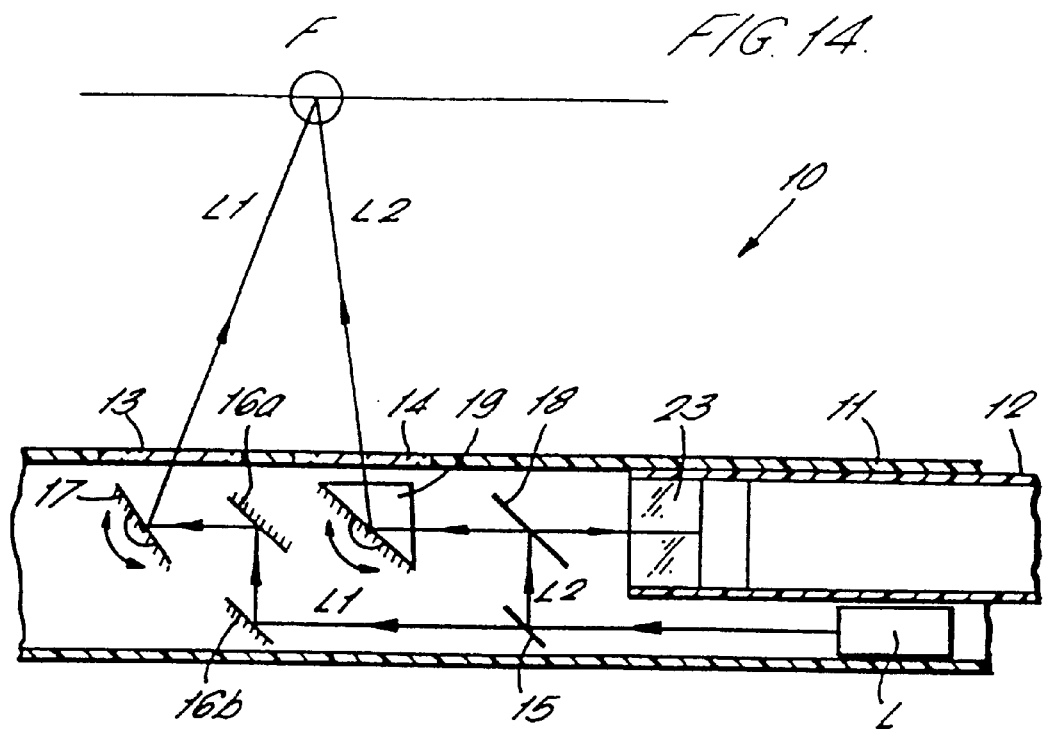
FIG. 14 shows in cross section, the distal end of a scope in accordance with a second embodiment of the invention.

FIG. 14 illustrates a second embodiment of scope in accordance with the present invention. As before, the scope 10 consists of a conventional insertion tube 11 containing an inner tube 12 with a conventional image transmission system, such as a series of lenses 23. In this example, the scope 10 is provided with a pair of lateral viewing windows 13 and 14.

A laser source L, which in this case is illustrated as positioned within the insertion tube 11 provides a single laser beam which is split into two beams L1 and L2 by a conventional beam splitter 15 which is located in a fixed position in the path of the beam. The first laser beam L1 is directed by way of two further fixed position reflectors 16a and 16b to a pivotable reflector 17. The first laser beam L1 strikes the reflector 17 at its pivot point and is reflected so as to exit the insertion tube 11 through the first window 13. The position of the reflector 17 can be adjusted until the laser beam L1 strikes the target feature F at the desired location.

The second laser beam L2 is directed via a fixed position reflector 18 to a second pivotable reflector 19. The second laser beam L2 strikes the pivotable reflector 19 at its pivot point and the reflector 19 is also adjusted to direct the laser beam L2 out of the scope 10 through the second window 14 towards the target feature F.

In this example, the second pivot reflector 19 is shown as a prism whereas the first steerable reflector 17 is shown as a mirror. Likewise, the fixed position reflectors 16a and 16b are shown as mirrors. However, mirrors or prisms can be used in any desired combination.

The pivotable reflectors 17 and 19 are provided with control means and antibacklash devices in the same manner as described above and the scope is also used in the same manner. The target feature F is observed through the second window 14. Light received through this window 14 is reflected by the pivotable reflector 19 so as to pass directly through fixed reflector 19 and into the image transmission system in the inner tube 12 for transmission to the viewing means.

In a third embodiment of the invention illustrated in FIG. 15, a laser source L directs a laser beam at a pivotable beam splitter device 20. This device splits the beam into two laser beams L1 and L2. The first laser beam L1 passes through the beam splitter 20 and continues to strike a first steerable reflector 17, which directs the beam L1 through a first window 13 to the target feature F.

The second laser beam L2 is reflected by the pivotable beam splitter 20 so as to exit the insertion tube 11 through a second window 14. As before, position sensing means (not shown) are associated with reflector 17 and also with the beam splitter 20 and the beams L1,L2 each strike the respective reflector 17,20 at its pivot point. Thus, the pivot points define the first and second reference points and the datum line R.

The target feature F is viewed through a third viewing window 21 arranged proximally of the first and second windows 13,14. Light entering the window 21 is reflected by a further pivotable reflector 22 into the image transmission system within the inner tube 12 for transmission to the viewing means. The reflector 22 which receives the image is pivotable to enable to viewing axis V of the scope to be adjusted and thereby to ensure that the target feature F is in the centre of the scope's field of view. As before, data from the position sensing means associated with steerable reflectors 17 and 20 is transmitted to processing means for calculation of the required dimensions of the feature F.

Yet another alternative configuration is illustrated schematically in FIG. 16. In this example, a single laser source L directs a single laser beam L1 to a steerable reflector 17, striking it at its pivot point. The beam L1 is reflected by this reflector 17 through a first window 13 in order to strike the target feature F.

In this case a second laser beam is not provided. Instead, the viewing axis V of the scope is used to provide a reference axis which can be adjusted so as to intersect the first laser beam L1 at the target feature F as described below.

The target feature F is viewed through a second viewing window 14 and light received through this window 14 is diverted by a pivotable reflector 22 into the image transmission system within the second tube 12. In this example the light received passes through an objective lens 23 and a graticule 24 to an image-to-video converter 25, such as a charged coupled device (CCD).

In the same way as previous embodiments, reflectors 17 and 22 are pivotable and are associated with antibacklash devices and position sensing means. An image of the target feature F is viewed through the graticule 24 and the reflector 22 is pivoted until an image of the spot of light provided by the laser beam L1 on the target feature F is correctly centred on the graticule 24. At this point, the viewing axis V is positioned as shown in FIG. 16. In particular, the viewing axis V intersects the pivot point of the pivotable reflector 22 and is directed from that point to the spot of light produced by the laser beam L1 on the target feature. As before, a datum line R is defined by the pivot points of the two reflectors 17 and 22. Therefore, the viewing axis V is oriented in the same position relative to the datum line R as is the second laser beam L2 in the embodiment illustrated in FIG. 14. The present embodiment therefore produces an equivalent result to the FIG. 14 arrangement but requires only a single laser beam.

Turning now to FIG. 17, this embodiment employs two separate laser sources L, L' to produce two laser beams L1 and L2, thereby to avoid the use of a beam splitter. Like the embodiments of FIGS. 13 and 14, the second laser beam L2 is provided to define the reference axis, rather than using the viewing axis V as in FIG. 16.

The first laser source L produces a first beam L1 which is directed to a pivotable reflector 17, which diverts the beam L1 through a first window 13 towards the target feature F in the same way as previous embodiments.

The second laser source L' produces a second laser beam L2 and directs it via a pivotable beam splitter 20 to a fixed reflector 19 which diverts the beam through a second viewing window 14 to the target feature F. The target feature F is viewed through the second viewing window 14 and light received through this window 14 is diverted by the fixed reflector 19 into the image transmission system.

In this system, the viewing axis V is fixed as shown by the chain line and therefore the target feature F may not always be in the centre of the field of view.

In this embodiment the pivot points of the two pivotable reflectors 17,18 define the datum line as before but the pivot point of the second reflector 18 does not define the second reference point because it does not form the last point from which the second laser beam L2 is directed towards the target feature F. Consequently, the angle of the second laser beam L2 as it exits the scope relative to the datum line R is not measured directly but it can be calculated with reference to the angle of the pivotable reflector 18 relative to the datum line. Calculations based upon this angle of the reflector 18 can also be used to determine the theoretical separation S between the first and second laser beams at the datum line.

An alternative dual laser source arrangement is illustrated in FIG. 18. This is very similar to the arrangement shown in FIG. 17 although here the beam splitter 18 is fixed and the reflector 19 is pivotable. Therefore, the first and second reference points are defined by the pivot points of the pivotable reflectors 17,19 so that the separation S is known and the angle of the second laser beam L2 relative to the datum line R can be measured directly.

The skilled person will appreciate that the various arrangements shown in FIGS. 6–18 are in no way exhaustive of all the possible arrangements. Any other convenient configuration may of course be used to embody a measuring system in accordance with the present invention.

For example, to avoid the use of multiple reflectors and for use with a flexible type insertion tube, the laser beams L1 and L2 may be delivered to the final stage reflectors by accurately positioned optical fibres. In addition, although the embodiments described are all scopes for lateral viewing, a measuring system in accordance with the present invention may also be incorporated into a scope for viewing in the direction of the longitudinal axis of the insertion tube.

The position sensing means associated with the steerable elements in the aforementioned embodiments may be of any suitable type. As mentioned above, one example of suitable position sensing means is a linear voltage displacement transducer (LVDT). Another possibility is a Moiré fringe device of the type used, for example, in digital micrometers. This type of device employs two diffraction gratings, one oriented at an angle to the other, and a photocell. Movement of one grating relative to the other produces pulses in the photocell which can be decoded to indicate the degree of movement. The position sensing means could be of miniaturised form for location at the distal end of the scope 10 in proximity to the appropriate pivotable elements.

Other alternatives are a variable resistor potentiometer, a variable reluctance transformer and an inductosyn.

From the foregoing it will be apparent that the present invention provides an improved optical scope which can be used to determine the object distance of a feature viewed through the scope more reliably than prior art systems and which can also be used to measure dimensions directly.

What is claimed is:

1. An optical scope for viewing a feature at an inaccessible location, comprising a tube having a distal end which is insertable in use into an inaccessible location and a proximal end connected to a housing; an optical system for gathering an image of a feature and relaying the image to a viewing means; means to direct a laser beam to a first reference point in the distal end of the tube; a first reflector mounted in the distal end of the tube for rotation about the first reference point and being operable to change the direction of the laser beam so as to direct the beam out of the scope to a target feature; a second reflector mounted in the distal end of the tube for rotation about a second reference point and being operable to change the direction of a reference axis intersecting the second reference point so as to cause the axis to intersect the laser beam at the target feature; control means actuable at the proximal end of the scope to rotate the first and second reflectors about the first and second reference points; position sensing means to detect movement of the first and second reflectors, and antibacklash means associated with the control means, which antibacklash means combats backlash by opposite direction reflector biasing.

2. An optical scope as claimed in claim 1, wherein the control means for each reflector comprises a mechanical linkage extending between the reflector and a rotatable control collar mounted on the housing.

3. An optical scope as claimed in claim 2, wherein the mechanical linkage comprises a pullwire.

4. An optical scope as claimed in claim 3, wherein the pullwire is looped around a wheel, whose axis is spring biased in the proximal direction, to provide two pullwire limbs, the first limb is attached to the reflector on one side of its pivot point, the second limb is attached to the reflector on the other side of its pivot point and first and second position sensing means are associated with the first and second limbs respectively.

5. An optical scope as claimed in claim 1, wherein the antibacklash means comprises spring means biasing each reflector in opposition to the control means.

6. An optical scope as claimed in claim 5, wherein the antibacklash means further comprises a friction braked wheel to which the proximal end of the pullwire is secured.

7. An optical scope as claimed in claim 5, wherein the antibacklash means further comprises a first cylinder located, and constrained to move axially, in the housing and to which the proximal end of the pullwire is secured, a second cylinder located proximally of the first cylinder and also constrained to move axially, spring means urging the first and second cylinders towards each other, a rotatable actuating collar linked to the first and second cylinders to move the cylinders axially upon rotation of the collar and spring means urging the collar axially against a fixed part of the housing.

8. An optical scope as claimed in claim 5 wherein said spring means is positioned distal to said first reflector and said anti-backlash means further comprises an anti-backlash mechanism positioned proximal to said first reflector.

9. An optical scope as claimed in claim 1 further comprising means to direct a second laser beam to the second reference point, whereby the reference axis is defined by the second laser beam.

10. An optical scope as claimed in claim 1, wherein the scope has a viewing axis intersecting the second reference point whereby the reference axis is defined by the viewing axis.

11. An optical scope as claimed in claim 10, wherein a graticule is mounted in the image transmission system, whereby when an image of a feature is aligned with the centre of the graticule the viewing axis is positioned so as to intersect the feature.

12. An optical scope as claimed in claim 1, wherein the means to direct the first laser beam to the first reference point comprises at least one optical fibre.

13. An optical scope as claimed in claim 12 wherein the means to direct the first laser beam to the first reference point further comprises at least one reflector mounted in the path of the beam.

14. An optical scope as claimed in claim 9, wherein the means to direct the second laser beam to the second reference point comprises at least one optical fibre.

15. An optical scope as claimed in claim 14, wherein the means to direct the second laser beam to the second reference point further comprises at least one reflector mounted in the path of the beam.

16. An optical scope as claimed in claim 1, wherein the position sensing means is located in the housing.

17. An optical scope as claimed in claim 1, wherein the position sensing means comprises a linear voltage displacement transducer.

18. An optical scope as claimed in a claim 1, wherein the position sensing means comprises a Moire fringe device.

19. An optical scope as claimed in claim 1, wherein the position sensing means comprises a variable resistor potentiometer.

20. An optical scope as claimed in claim 1, wherein the position sensing means comprises a variable reluctance transformer.

21. An optical scope as claimed in claim 1, wherein the position sensing means comprises an inductosyn.

22. An optical scope as claimed in claim 1 wherein said anti-backlash means includes an anti-backlash mechanism positioned proximal to the first reflector.

23. An optical scope as claimed in claim 22 wherein said anti-backlash mechanism is positioned in the housing.

24. An apparatus for determining a dimension of a feature at an inaccessible location, comprising an optical scope as claimed in claim 1, viewing means for receiving an image relayed by the optical system of the optical scope and processing means for receiving data from the position sensing means and calculating a dimension of the feature from the data.

25. Apparatus as claimed in claim 24, wherein the viewing means comprises a camera and a monitor for displaying the image received by the camera.

26. Apparatus as claimed in claim 24 wherein said control means includes a linkage connected with said first reflector, and said position sensing means is in sensing communication with said linkage at a position between said first reflector and an anti-backlash mechanism of said anti-backlash means.

27. An optical scope for viewing a feature at an inaccessible location, comprising a tube having a distal end which is insertable in use into an inaccessible location and a proximal end connected to a housing; an optical system for gathering an image of a feature and relaying the image to a viewing means; means to direct a laser beam to a first reference point in the distal end of the tube; a first reflector mounted in the distal end of the tube for rotation about the first reference point and being operable to change the direction of the laser beam so as to detect movement of the first and second reflectors, and antibacklash means associated with the control means direct the beam out of the scope to a target feature; a second reflector mounted in the distal end of the tube for rotation about a second reference point and being operable to change the direction of a reference axis intersecting the second reference point so as to cause the axis to intersect the laser beam at the target feature; control means actuable at the proximal end of the scope to rotate the first and second reflectors about the first and second reference points; position sensing means to detect movement of the first and second reflectors, and antibacklash means associated with the control means, wherein the antibacklash means comprises spring means biasing each reflector in opposition to the control means, and wherein the antibacklash means further comprises a recirculating ball screw device to which the proximal end of the pullwire is secured.

28. An optical scope for viewing a feature at an inaccessible location, comprising a tube having a distal end which is insertable in use into an inaccessible location and a proximal end connected to a housing; an optical system for gathering an image of a feature and relaying the image to a viewing means; means to direct a laser beam to a first reference point in the distal end of the tube; a first reflector mounted in the distal end of the tube for rotation about the first reference point and being operable to change the direction of the laser beam so as to direct the beam out of the scope to a target feature; a second reflector mounted in the distal end of the tube for rotation about a second reference point and being operable to change the direction of a reference axis intersecting the second reference point so as to cause the axis to intersect the laser beam at the target feature; control means actuable at the proximal end of the scope to rotate the first and second reflectors about the first and second reference points; position sensing means to detect movement of the first and second reflectors, and antibacklash means associated with the control means wherein said control means includes a linkage connected with said first reflector, and said position sensing means includes a sensor positioned in line with said linkage between said first reflector and an anti-backlash mechanism of said anti-backlash means.

29. An optical scope for viewing a feature at an inaccessible location, comprising a tube having a distal end which is insertable in use into an inaccessible location and a proximal end connected to a housing; an optical system for gathering an image of a feature and relaying the image to a viewing means; means to direct a laser beam to a first reference point in the distal end of the tube; a first reflector mounted in the distal end of the tube for rotation about the first reference point and being operable to change the direction of the laser beam so as to direct the beam out of the scope to a target feature; a second reflector mounted in the distal end of the tube for rotation about a second reference point and being operable to change the direction of a reference axis intersecting the second reference point so as to cause the axis to intersect the laser beam at the target feature; control means actuable at the proximal end of the scope to rotate the first and second reflectors about the first and second reference points; position sensing means to detect movement of the first and second reflectors, and antibacklash means associated with the control means, wherein said anti-backlash means includes an anti-backlash mechanism positioned proximal to said first and second reflectors and proximal to said position sensing means.

* * * * *